(12) United States Patent
Hubsch et al.

(10) Patent No.: US 7,491,693 B2
(45) Date of Patent: Feb. 17, 2009

(54) HDL FOR THE TREATMENT OF STROKE AND OTHER ISCHEMIC CONDITIONS

(75) Inventors: Alphonse Hubsch, Laetti (CH); Markus G. Lang, Devon, PA (US)

(73) Assignee: CSL Behring AG, Bern (CH)

( * ) Notice: Subject to any disclaimer, the term of this patent is extended or adjusted under 35 U.S.C. 154(b) by 94 days.

(21) Appl. No.: 11/744,780

(22) Filed: May 4, 2007
(Under 37 CFR 1.47)

(65) Prior Publication Data

US 2008/0108550 A1 May 8, 2008

Related U.S. Application Data

(63) Continuation of application No. 10/487,224, filed as application No. PCT/EP02/09294 on Aug. 20, 2002, now abandoned.

(60) Provisional application No. 60/313,605, filed on Aug. 20, 2001.

(30) Foreign Application Priority Data

Aug. 20, 2001 (EP) .................................. 01120026

(51) Int. Cl.
*A61K 38/17* (2006.01)
*C07K 14/775* (2006.01)

(52) U.S. Cl. .......................................... 514/2; 530/359

(58) Field of Classification Search .................. 530/359
See application file for complete search history.

(56) References Cited

U.S. PATENT DOCUMENTS 5,780,592 A 7/1998 Mullner et al.

FOREIGN PATENT DOCUMENTS

| WO | WO 01/03705 A | 1/2001 |
|---|---|---|
| WO | WO 01/13939 A | 3/2001 |
| WO | WO 01/38395 A1 | 5/2001 |

OTHER PUBLICATIONS

Excerpt from MacQuarie Australia's National Dictionary; 2 pages, 1998.
Excerpt from Stedman's Medical Dictionary; pp. 924, 2000.
Excerpt from Black's Medical Dictionary; pp. 497, 1984.
Excerpt from Gould Medical Dictionary; pp. 798, 1972.
Orekhov, A.N. et al.; "Artificial HDL as an anti-atherosclerotic drug;" The Lancet; Nov. 17, 1984; pp. 1149-1150.
Dansky, Hayes M. et al.; "High-Density Lipoprotein and Plaque Regression: The Good Cholesterol Gets Even Better;" Circulation, Journal of the American Heart Association; 1999; vol. 100; pp. 1762-1763.
Badimon, J.J. et al.; "Regression of Atherosclerotic Lesions by High Density Lipoprotein Plasma Fraction in the Cholesterol-fed Rabbit;" Journal of Clinical Investigation; Apr. 1990; vol. 85; pp. 1234-1241.
Cockerill et al. "High-density lipoproteins rescue end-stage organ failure in a rat model of haemorraghic shock," *J. Submicroscopic Cyt. Path.* 32(3): 353, 2000.
Klimov, et al., "Effect of high density lipoproteins on permeability of rabbit aorta to low density lipoproteins," *Atherosclerosis*, 1985, 55(2):217-23.
Lerch, et al., "Reconstituted high density lipoprotein (rHDL) modulates platelet activity in vitro and ex vivo," *Thromb Haemost.* 1998, 80(2):316-20.

*Primary Examiner*—Tekchand Saidha
(74) *Attorney, Agent, or Firm*—Foley & Lardner LLP; R. Brian McCaslin

(57) ABSTRACT

The present invention relates to a method for the prophylaxis and/or treatment of stroke and other ischemic injury, wherein HDL is administered to a subject in need thereof, particularly by intravenous infusion.

13 Claims, 3 Drawing Sheets

HDL FOR THE TREATMENT OF STROKE AND OTHER ISCHEMIC CONDITIONS

INFORMATION ON RELATED APPLICATIONS

This application is a continuation of U.S. application Ser. No. 10/487,224, filed Aug. 2, 2004 now abandoned, which is a U.S. National Stage of PCT/EP2002/09294, filed Aug. 20, 2002, which claims priority to European Application No. 01120026.8, filed Aug. 20, 2001, and U.S. Provisional Application No. 60/313,605, filed Aug. 20, 2001, the disclosures of which are incorporated by reference herein in their entireties.

DESRIPTION

The present invention relates to a method for the prophylaxis and/or treatment of stroke and other ischemic conditions, wherein HDL particles, as exemplified by reconstituted HDL (rHDL) particles are administered to a subject in need thereof, particularly by intravenous infusion.

Stroke can be classified into thrombo-embolic and hemorrhagic forms and is the third largest cause of death in western countries, after heart disease and cancer. In the United States each year 600 000 people suffer a new or recurrent stroke (about 500 000 are the first attacks) and approximately 29% of them die within the first year (1). The incidence of stroke increases with age, and in the elderly it is the leading cause of serious, long-term disability in the US accounting for total costs of 51.3 billion $/year (1). Although the death rate from stroke has been decreasing in recent years, largely due to the increased awareness and better control of risk factors such as hypertension, hypercholesterolemia, arrhythmia or diabetes, the actual number of stroke deaths is rising because of an increasing elderly population. However, when prevention measures fail only limited and risky thrombolytic approaches exist, e.g. t-PA (tissue plasminogen activator). Neuronal protection could become a new and safer strategy for stroke treatment in the future (2-4).

One common cause of circulatory shock is severe blood loss associated with trauma, Despite improvements in intensive care medicine, mortality from hemorrhagic shock remains high (5, 6). Thus, there is still a great need for new approaches to improve therapy and outcome of patients with hemorrhagic shock (6). In clinical practice, hemorrhagic shock leads to a delayed vascular decompensation (resulting in severe hypotension) and, in approximately 25% of patients, in the dysfunction or failure of several organs including lung, kidney, gut, liver and brain (7). Organ dysfunction can also occur from an ischemic event, caused by a reduction in blood supply as a result of a blockage as distinct from a hemorrhage. There is also evidence that reperfusion (during resuscitation) also plays a role in the pathophysiology of the multiple organ dysfunction syndrome (MODS)(8).

According to WO 01/13939 and (21) rHDL used in a rat hemorrhagic shock model demonstrated a significant reduction of organ damage. Hemorrhagic shock comprises a generalized reduction in blood supply to the whole body which results in hypoxic damage that affects all organs and tissues. In contrast, ischemia describes a localized depletion of blood supply to specific organs and tissues, resulting in a rapid onset of anoxia in these affected regions The mechanisms of damage are therefore quite distinct.

rHDL has been shown to stimulate cholesterol efflux from peripheral cells in a process better known as reverse cholesterol transport. Furthermore, rHDL dose-dependently binds bacterial lipopolysaccharides (LPS) and inhibits LPS-induced cytokine production as well as adherence of PMNs (polymorphonuclear leukocytes) to endothelial cells (21). rHDL has anti-inflammatory and free oxygen radical scavenger activity. rHDL also decreases the rate and the extent of platelet aggregation. More recently it was demonstrated that rHDL acutely restores endothelial function and in turn normalizes blood flow in hypercholesterolemic patients by increasing nitric oxide bioavailability as determined by forearm plethysmography (9).

The pathophysiology of stroke is characterized by a wide range of homoeostatic, hemodynamic and metabolic abnormalities such as thrombus formation, impaired endothelial function and an activated inflammation cascade, i.e. increased cytokine production and expression of adhesion molecules (10-15). Another hallmark of stroke is the augmented oxidative stress after reperfusion which is thought to play a detrimental role in the progression of the disease.

Prolonged ischemia results in an elevation of intracellular $Ca^{++}$ and the consequent activation of proteases and phospholipases results in formation of numerous potentially damaging products of membrane lipid breakdown. These include arachiodonic acid metabolites, which, in the presence of oxygen during reperfusion, provide a source of free radical formation (e.g. superoxide and hydroxyl anions). These free radicals induce blood brain barrier destruction and neuronal apoptosis and/or necrosis. Apoptosis is a form of cell death that eliminates compromised or superfluous cells with no inflammatory response and is differentiated from necrosis by many morphological and biochemical characteristics. The feature of apoptosis can be found in both neurons and glia after ischemic injuries. Neurons in the ischemic penumbra, that are not exposed to lethal ischemia, may undergo delayed apoptosis (16). The so called penumbra is a brain area where blood flow is reduced to a level that interrupts neuronal function and the consequent electrical activities, yet permits maintenance of membrane pumps and preservation of ion gradients. This brain area has two characteristics that explain its potential clinical importance: 1) the interruption of clinical and electrical function that characterizes this area is fundamentally reversible, but 2) the reversibility is time-limited and linked to reperfusion.

Surprisingly, it was found that the size of the lesions in animal models for stroke (excitotoxicity and cerebral artery occlusions) is reduced by administration of HDL. These data show that HDL can improve the outcome following excitotoxic and ischemic/reperfusion neuronal damage, particulary apoptosis and/or necrosis in the ischemic area and in the penumbra. Further, it was shown in an animal model for hemorrhagic shock that HDL reduces the PMN infiltration and prevents organ injury and dysfunction. At present, the mechanism of action is unknown. While not wishing to be bound by theory, it is possible that HDL might act as a free oxygen radical scavenger, vasodilator, e.g. via improvement of NO bioavailability resulting in an improvement of collateral blood flow or it may exhibit an anti-inflammatory effect. Thus, HDL may act as a neuroprotective drug particularly in cerebrovascular diseases. It might also work by a combination of all these activities, achieving a clinical efficacy not yet seen in current therapies.

The invention generally relates to the use of HDL for the prophylaxis and/or treatment of ischemia or reperfusion injury. Ischemia to an organ occurs as a result of interruption to its blood supply, and in its broadest sense may result in organ dysfunction or damage, especially heart, cerebral, renal, liver or lung. It is a local event/interruption that leads to complete or partial and in some cases reversible damage. Reperfusion injury occurs as a consequence of rapid return of oxygenated blood to the area following ischemia and is often referred to in cardiovascular and cerebral misadventures.

Thus, a subject matter of the present invention is the use of HDL for the manufacture of an agent for the prophylaxis and/or treatment of ischemia or reperfusion injury. Particularly, HDL may be used for the prophylaxis and/or treatment of a disorder selected from ischemic stroke, ischemic tissue injury, e.g. ischemic injury of organs, cardiac ischemia, cardiac reperfusion injury and complications resulting from organ transplantation, e.g. kidney, heart and liver or cardiopulmonary bypass surgery and other disorders, Even more surprisingly, it has been found that HDL can have a beneficial effect when a transient or a permanent occlusion is in place. As a result, it is not a prerequisite for efficacy that the clot or other entity causing the occlusion be dissolved or otherwise removed. Moreover, administration of HDL shows benefits even 6 or more hours after an ischemic event. A further surprising observation has been the beneficial effect of HDL administration before an ischemic event.

A further embodiment of the invention relates to the use of HDL for prophylaxis and/or treatment of transient ischemic attacks (TIA). TIAs are common and about one third of those affected will develop a stroke some time later. The most frequent cause of TIA is the embolization by a thrombus from an atherosclerotic plaque in a large vessel (typically a stenosed atheromatous carotid artery). As HDL has anti-atherosclerotic properties, as shown in studies looking at endothelial function through the restoration of bioavailability of nitric oxide, regulation of vascular tone and structure (9) it is thought that HDL may play a role in stabilizing an atheromatous plaque causing TIAs thereby reducing the risk of a major stroke. Current therapy for TIAs include antiplatlet therapy, aspirin, ticlopidin and surgical intervention such as endoarterectomy. However, none of these provide, as yet, a substantial reduction in morbidity.

Yet a further embodiment relates to the prophylactic administration of HDL to risk patient groups such as patients undergoing surgery. Administration of HDL may reduce the incidence and/or severity of new strokes Prophylactic administration of HDL could also be useful in patients with TIAs, atrial fibrillation and asymptomatic carotid stenosis.

The use of HDL for the treatment of the above diseases, particularly for the treatment of stroke and transient ischemic attacks fulfills an as yet unmet clinical need. It provides a clinically effective neuroprotective therapy for individuals with traumatic brain injury.

Figure 1:
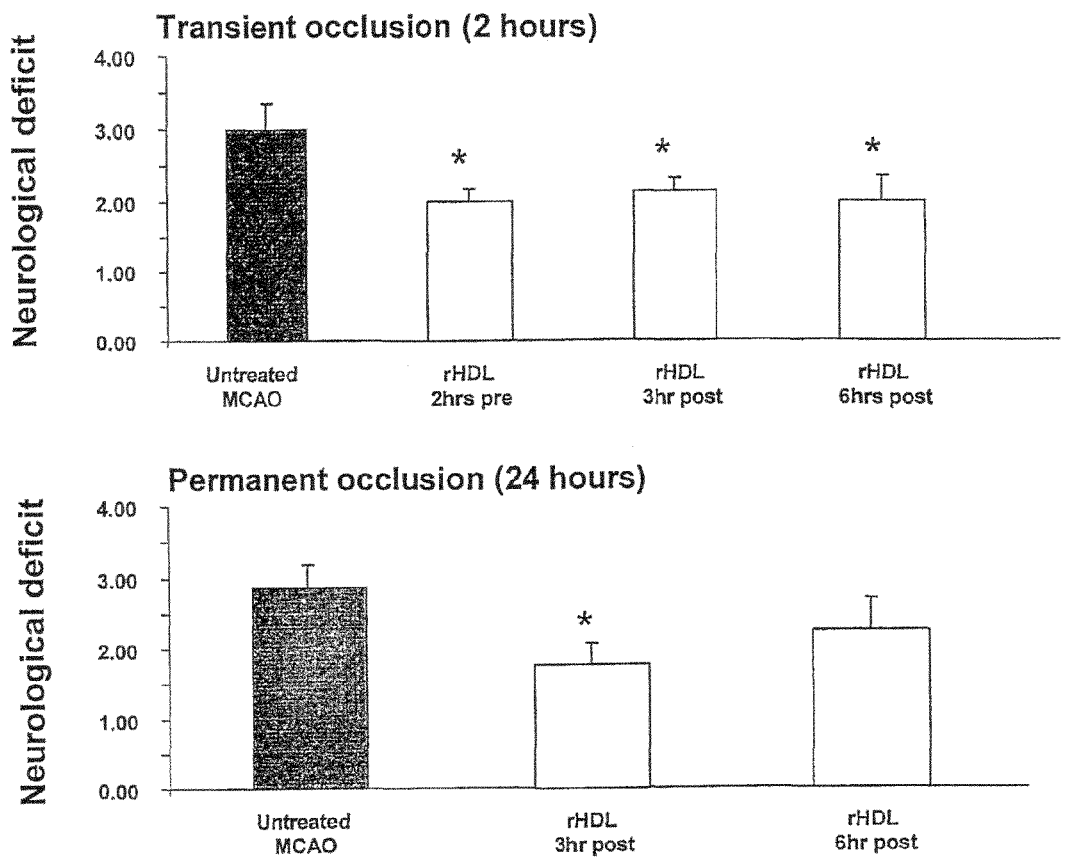
FIG. 1 shows the combined effect of rHDL treatment upon performance in four neurological tests (forelimb flexion, torso twisting, lateral push and mobility) by rats with MCA occlusions FIG. 2 graphically depicts the effect of rHDL on the infarct area caused by a transient MCA occlusion.

The term "HDL" as used in the present invention relates to particles similar to high density lipoproteins and comprises nascent HDL or reconstituted HDL (rHDL) or any mixture thereof. Such particles can be produced from a protein or peptide component, and from lipids. The term "HDL" also includes within its breadth any recombinant HDL or analogue thereof with functional relationship to nascent or reconstituted HDL.

The proteins are preferably apolipoproteins, e.g. human apolipoproteins or recombinant apolipoproteins, or peptides with similar properties. Suitable lipids are phospholipids, preferably phosphatidyl choline, optionally mixed with other lipids (cholesterol, cholesterol esters, triglycerides, or other lipids). The lipids may be synthetic lipids, naturally occurring lipids or combinations thereof.

Administration of HDL may result, on one hand, in a short term effect, i e. an immediate beneficial effect on several clinical parameters is observed and this may occur not only within 3 hours of onset of stroke, but even 6 hours or possibly even longer and, on the other hand, a long term effect, a beneficial alteration on the lipid profile may be obtained. Furthermore, HDL resembles very closely substances naturally occuring in the body and thus the administration of HDL is free of side effects. HDL is preferably administered by infusion, e.g. by arterial, intraperitoneal or preferably intravenous injection and/or infusion in a dosage which is sufficient to obtain the desired pharmacological effect. For example, HDL may be administered before the start of ischemia (if foreseeable, e.g. before an organ transplantation) and/or during ischemia, before and/or shortly after reperfusion, particularly within 24 h-48 h.

The HDL dosage ranges preferably from 10-200 mg, more preferably 40-80 mg HDL (weight based on apolipoprotein) per kg body weight per treatment. For example, the dosage of HDL which is administered may be about 20-100 mg HDL per kg body weight (weight based on apolipoprotein) given as a bolus injection and/or as an infusion for a clinically necessary period of time, e.g. for a period ranging from a few minutes to several hours, e.g. up to 24 hours. If necessary, the HDL administration may be repeated one or several times.

Reconstituted high density lipoprotein (rHDL) may be prepared from human apolipoprotein A-I (apoA-I), e.g. isolated from human plasma, and soybean-derived phosphatidylcholine (PC), mixed in molar ratios of approximately 1:150 apoA-1:PC.

According to the present invention, an HDL, e.g. nascent HDL, rHDL, recombinant HDL or an HDL-like particle is particularly preferred which has a molar ratio of protein (e.g. apolipoprotein A-1) and phospholipid in the range of 1:50 to 1:250, particularly about 1:150. Further, rHDL may optionally contain additional lipids such as cholesterol, cholesterol esters, triglycerides and/or sphingolipids, preferably in a molar ratio of up to 1:20,e.g. 1:5 to 1:20 based on the apolipoprotein. Preferred rHDL is described in EP-A-0663 407.

The administration of HDL may be combined with the administration of other pharmaceutical agents such as thrombolytic agents, anti-inflammatory agents, neuro- and/or cardioprotective agents.

Furthermore, the present invention relates to a method for prophylaxis and/or treatment of ischemia or reperfusion injury comprising administering a subject in need thereof an effective amount of HDL. Preferably, HDL is administered to a human patient.

Further, the present invention shall be explained in detail by the following examples:

EXAMPLE 1

Excitotoxic Lesion

Experiments were performed in Sprague-Dawley rats anesthetized with chloral hydrate (400 mg/kg ip). A femoral vein was cannulated for infusion of rHDL. Rats were placed into a stereotaxic apparatus and, after a midline incision, received a unilateral injection of N-methyl-D-aspartate (NMDA) or vehicle into the right striatum: coordinates: 0.2 mm posterior, 3 mm lateral, 5.5 mm ventral to the bregma. Five minutes after insertion of the needle the solution was injected over a period of 6 minutes using a Hamilton syringe pump at a rate of 0.5 ml/min. 5 minutes after injection has been completed, the needle was removed.

In this series of experiments rats received intravenous infusion of saline (n=5) (5 µl/min) over 4 h. After 2 h, unilateral injection of NMDA (75 nM in 3 ml of phosphate-buffered saline pH 7.4) was performed into the right striatum. After twenty-four hours rats were sacrificed and the brain was removed for histological analysis. In another group of experiments, rats received intravenous infusion of rHDL (n=5) (5 µl/min) at a dose of 120 mg/kg over 4 h. After 2 h, unilateral injection of NMDA (75 nM in 3 ml of phosphate-buffered saline pH 7.4) was applied into the right striatum and intravenous infusion of rHDL continued for an additional 2 h. Twenty-four hours later the rats were sacrificed and the brain was removed for histological analysis. The results are shown in Table 1.

TABLE 1 lesion volume in mm$^3$

| rat | control | rHDL |
| --- | --- | --- |
| 1 | 50.27 | 16.54 |
| 2 | 47.05 | 18.86 |
| 3 | 41.28 | 17.44 |
| 4 | 38.5 | 17.51 |
| 5 | 51.66 | 19.86 |
| n | 5 | 5 |
| MEAN | 45.75 | 18.04 |
| SD | 5.69 | 1.31 |
| SEM | 2.55 | 0.59 |

In this experiment a dramatic reduction of the brain necrotic volume in rHDL treated animals by 60.6% compared to controls was observed.

In a further series of experiments rHDL (120 mg/kg) or placebo (saline) infusion was administered over 4 h starting 3 h after NMDA injection. The infarct size was measured histologically after 24 h. The results are shown in Table 2.

TABLE 2

| | Saline + NMDA lesion vol. (mm$^3$) | rHDL + NMDA lesion vol. (mm$^3$) |
| --- | --- | --- |
| | 175 | 77 |
| | 101 | 83 |
| | 105 | 133 |
| | 180 | 121 |
| | 149 | 51 |
| | 115 | 66 |
| mean | 137 | 88 |
| SD | 35 | 32 |
| % reduction | | −36% |
| p (Students t test) | | 0.03 |

In this experiment a reduction of infarct size by 36% was found.

EXAMPLE 2

Middle Cerebral Artery Occlusion 2.1 Administration Before Occlusion

Experiments were performed in Sprague-Dawley rats anesthesized with chloral hydrate (400 mg/kg ip). The trachea were cannulated and the animals were mechanically ventilated with air and supplemental oxygen to maintain blood gases within normal ranges. Rectal temperature was continually monitored and maintained at 37° C. Catheters were placed into the femoral artery to measure systemic blood pressure and to monitor blood gases. A femoral vein was cannulated for infusion of drug A neck midline incision was made and the right common carotid artery was exposed. Following coagulation of its branches, the external carotid artery (ECA) was distally opened. A nylon thread (diameter 0.22 mm) which has a distal cylinder of silicon (2 mm long, diameter 0.38 mm) of thermofusible glue was inserted in the lumen of ECA and advanced into the internal carotid artery up the origin of MCA. To restore the MCA blood flow, the nylon thread was removed and cut thirty minutes later.

Histological Analysis:

Twenty-four hours after the surgery euthanasia was performed. The brains were rapidly removed, frozen in isopentane at −50° C. and stored at −80° C. Cryostat cut coronal brain sections (20 µm) were stained with thionine and analyzed using an image analyzer. The lesioned areas were delimited by the paleness of histological staining in altered tissue compared to the color of healthy tissue. Regions of interest were determined through the use of a stereotaxic atlas for the rat and an image analysis system was used to measure the lesioned area.

In this series of experiments rats received an intravenous infusion of saline (n=5) (5 µl/min) over 4 h. After 2 h the MCA of rats was occluded for 30 minutes followed by reperfusion. After twenty-four hours, rats were sacrificed for histological analysis of the brain. In another group of experiments, rats received intravenous infusion of rHDL (n=5) (5 µl/min) at a dose of 120 mg/kg over 4 h. After 2 h the MCA of rats were occluded for 30 minutes followed by reperfusion. Twenty-four hours later the rats were sacrificed for histological analysis of the brain. The results are shown in Table 3.

In the MCA occlusion model, the following results were obtained:

TABLE 3

Lesion volume in mm$^3$

| rat | control | rHDL |
| --- | --- | --- |
| 1 | 158.94 | 54.18 |
| 2 | 229.78 | 35.27 |
| 3 | 201.52 | 37.64 |
| 4 | 193.02 | 34.64 |
| 5 | 210.24 | 76.74 |
| n | 5.00 | 5.00 |
| MEAN | 198.70 | 47.69 |
| SD | 26.08 | 18.11 |
| SEM | 11.66 | 8.10 | rHDL reduced brain necrotic volume by 76% as compared to control rats 2.2 Administration After Occlusion rHDL was administered 3 h after injury in the MCAo (middle cerebral artery occlusion) model. In 12 rats temporary occlusion of the middle cerebral artery (MCA) was attained by inserting a nylon thread through the carotid artery and blood flow was restored 30 minutes later. After 3 hours they received an intravenous infusion of either rHDL (120 mg/kg over 4 h, 6 ml/kg over 4 h) or saline (6 ml/kg over 4 h). The rats were randomly assigned to the rHDL or the control group. In four additional rats the same procedure of MCA occlusion was performed but the nylon thread was halted in the internal carotid artery without interfering with carotid blood flow, and was removed thirty minutes later (Sham MCAO group). After 3 hours two rats of this group received rHDL and two received saline intravenously (6 ml/kg over 4 h). 24 h later, all rats were sacrificed and the brains were removed for histological analysis The necrotic area was delimited by the paleness of the histological staining as compared to the color of healthy tissue. Regions of interest were determined by use of a stereotaxic atlas for the rat and an image analysis system (NIH Image) was used to measure the necrotic area.

In the sham MCAO group there was no lesion.

After MCA occlusion in the other 12 rats treated intravenously with saline or rHDL, the results from the image analysis are presented in Table 4. The results show that infusion of rHDL 3 hours post occlusion resulted in a 60% reduction in infarct volume ($mm^3$).

TABLE 4 lesion area in $mm^3$

| rat | control | rHDL |
|---|---|---|
| 1 | 88.94 | 87 |
| 2 | 118.9 | 46.91 |
| 3 | 110.06 | 43.91 |
| 4 | 121.09 | 43.13 |
| 5 | 224.14 | 36.65 |
| 6 | 157.45 | 35.63 |
| mean | 136.8 | 48.9 |
| SD | 48.2 | 19.2 |
| % reduction | | 64% |
| p (Students t test) | | 0.0020 |

The necrotic volume was reduced by 64% as compared to control rats.

Conclusion

In both models, a dramatic reduction of the infarct volume was seen in rHDL treated animals, as compared to placebo treated controls: Excitotoxic model: 60.6% or 36% reduction of necrotic volume; MCA occlusion model: 76% or 60% reduction.

EXAMPLE 3

Administration of rHDL in a Rat Model for Stroke (MCA Occlusion Model)

Method 120 male Sprague-Dawley rats were used in this study. 100 rats received either a transient occlusion or permanent occlusion. 20 rats served as surgical and rHDL controls. rHDL (120 mg/kg/4 h) was infused starting 2 h before or 3 or 6 h after induction of stroke. The same thread occlusion method as in Example 2 was used.

Rats were grouped into three treatment arms. Group 1 received a prophylactic dose of rHDL 2 hours before receiving a transient MCA occlusion (2 hour) and continued receiving treatment during the occlusion The artery was then reperfused.

Group 2 received a transient MCA occlusion followed by reperfusion. Treatment with HDL was given either 3 hours or 6 hours later.

Group 3 received a permanent MCA occlusion and received treatment 3 hours or 6 hours after occlusion.

Following the above protocol the rats were examined for neurological change using four standard motor neurological tests, namely forelimb flexion, torso twisting, lateral push and mobility. The scores were added for each of the tests and the results presented in FIG. 1.

From this Figure it is clear that rHDL given both as a pretreatment and as a dose 3 or 6 hours post occlusion (both transient and permanent) resulted in a better neurological score than untreated rats.

Figure 2:
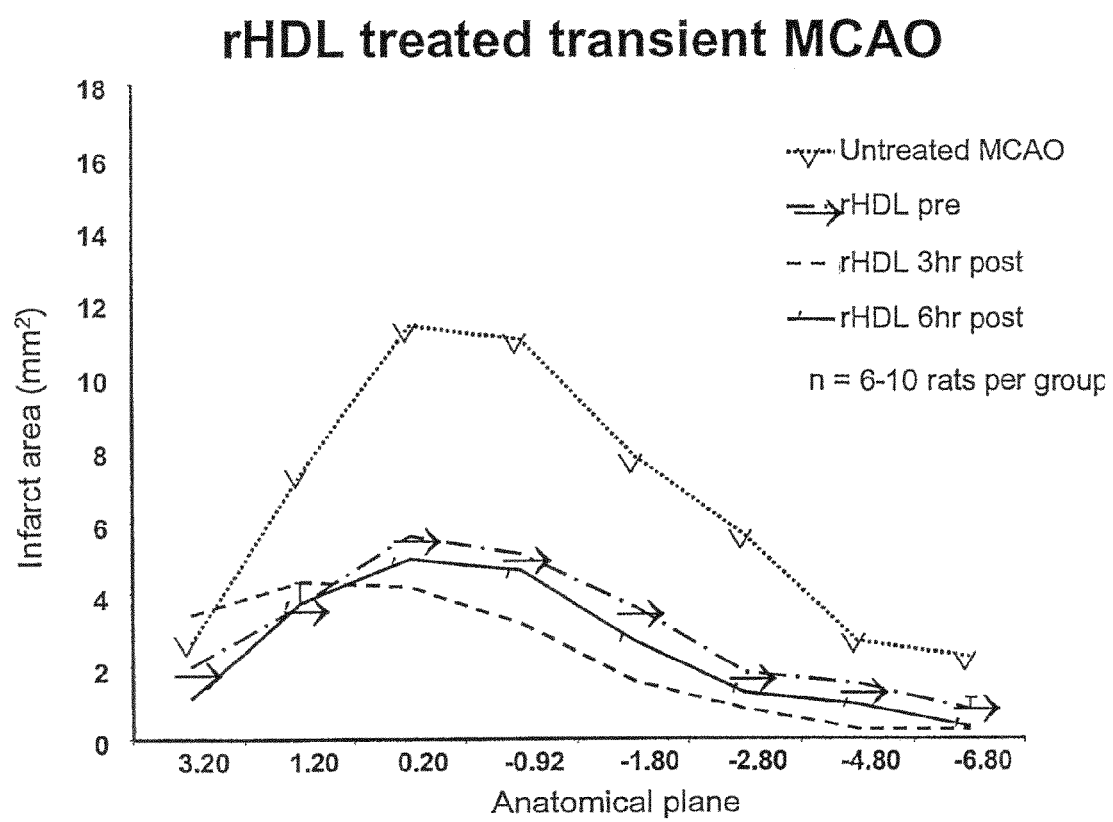
Figure 3:
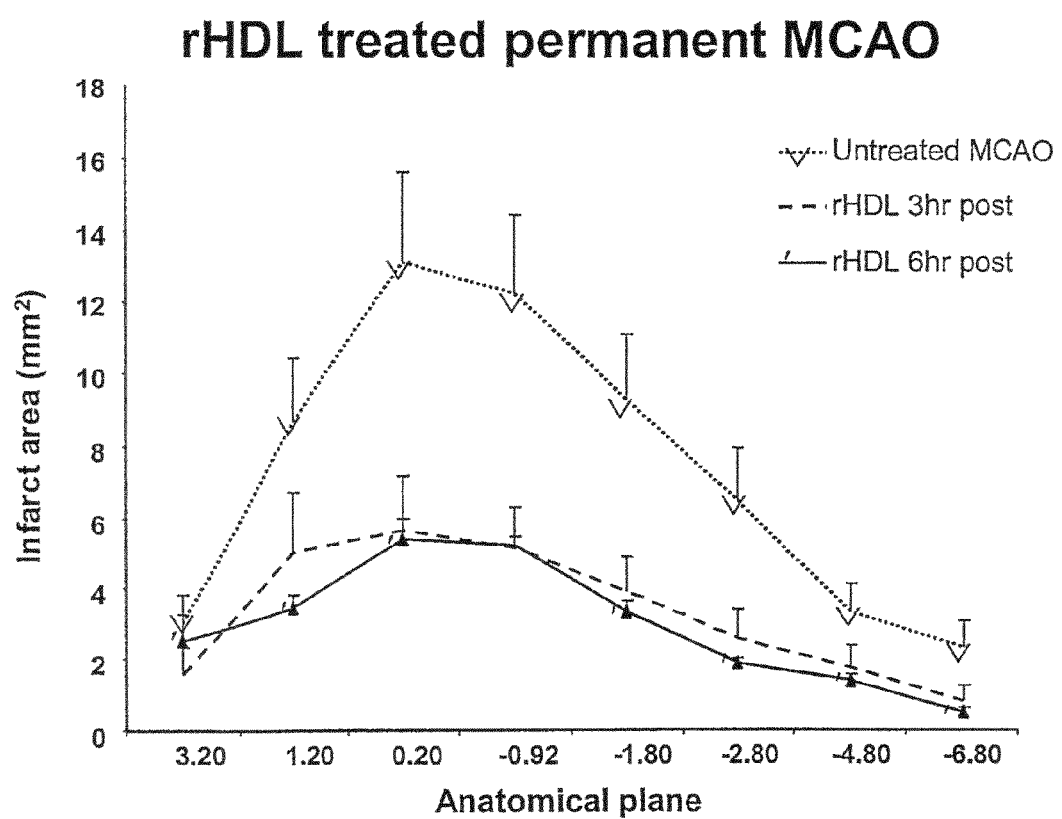
FIG. 3 graphically depicts the effect of rHDL on the infarct area caused by a permanent MCA occlusion.

Following the neurological analysis the rats were sacrificed and their brain removed. Sections of rat brain were examined using a ballistic light technique that measured infact area by the reflection of light. The results for rHDL treated permanent and transient MCAO are shown in FIGS. 2 and 3.

These graphs show that if rHDL is given to rats (i) 2 hours before occlusion there is a reduction in total infarct volume of 54% (ii) 3 hours post transient occlusion there is a reduction of 65% and (iii) 6 hours post transient occlusion a reduction of 62%. A similar reduction of 59% was observed for permanent occlusion at both treatment times.

Thus, the administration of rHDL is efficacious as a prophylactic treatment before occlusion and as a therapeutic treatment at two different points of time after occlusion. More particularly, a prophylactic and therapeutic treatment may be combined.

LITERATURE

1. American Heart Association (AHA), 2000
2. Hays S J. Therapeutic approaches to the treatment of neuroinflammatory diseases. Curr Pharm Des 4:335-348, 1998
3. Jean W C, Spellman S R, Nussbaum E S, Low W C, Reperfusion injury after focal cerebral ischemia: the role of inflammation and the therapeutic horizon. Neurosurgery 43:1382-1396, 1998
4. Barone F C, Feuerstein G Z. Inflammatory mediators and stroke: new opportunities for novel therapeutics. J Cereb Blood Flow Metab 19:819-834, 1999
5. Morgan W M, and Q'Neill J A. Hemorrhagic and obstructive shock in pediatric patients. New Horiz 6: 150-154, 1998
6. Demetriades D, Smith J S, Jacobson L E, Moncure M, Minei J, Nelson B J and Scannon P J, Bactericidal/permeability-increased protein (rBP121) in patients with hemorrhage due to trauma: results of a multicancer phase II clinical trial. RBP121 Acute Hemorrhage Trauma Study Group. J Trauma 46: 667-676, 1999
7. Regel G, Gotz M, Weltner T, Sturm J A and Tscherne H. Pattern of organ failure following severe trauma. World J Surg 20: 422-429, 1996
8. Cryer H G. Therapeutic approaches for clinical ischaemia and reperfusion injury. Shock 8: 26-32, 1997
9. Spieker L E, Sudano I, Lerch P G, Lang M G, Binggeli C, Corti R, Lüscher T F, Noll G. High-density lipoprotein restores endothelial function in hypercholesterolemic men. N Engl J Med, 2000. (in preparation)
10. Feuerstein G Z, Wang X, Barone F C. The role of cytokines in the neuropathology of stroke and neurotrauma. Neuroimmunomodulation 5:143-159, 1998
11. DeGraba T J. The role of inflammation after acute stroke: utility of pursuing anti-adhesion molecule therapy. Neurology 51:62-68, 1998
12. Benveniste E N Cytokine actions in the central nervous system. Cytokine Growth Factor Rev 9:259-275, 1998
13. Van Wagoner N J, Benveniste E N. Interleukin-6 expression and regulation in astrocytes. J. Neuroimmunol 100: 124-139, 1999
14. Touzani O, Boutin H, Chuquet J, Rothwell N. Potential mechanism of interleukin-1 involvement in cerebral ischemia. J Neuroimmunol 100:203-215, 1999
15. del Zoppo G, Ginis I, Hallenbeck J M, Iadecola C, Wang X, Feuerstein G Z. Inflammation and stroke: putative role for cytokines, adhesion molecules and iNOS in brain responses to ischemia. Brain Pathol 10:95-112, 2000

16. Du C, R Hu, C A Csernansky, C Y Hsu, D W Choi. Very delayed infarction after mild focal cerebral ischemia: A role for apoptosis? J Cereb Blood Flow Metab 16:195-201, 1996
17. Matsuda Y, Hirata K, Inoue N, Suematsu M, Kawahima S, Akita H, Yokoyama M. High density lipoprotein reverses inhibitory effect of oxidized low density lipoprotein on endothelium-dependent arterial relaxation. Circ Res 72(5): 1103-1109, 1993
18. Chander R, Kapoor N K. High density lipoprotein is a scavanger of superoxide anions. Biochem Pharmacol 40(7):1663-1665, 1990
19. Araujo F B, Barbosa D S, Hsin C Y, Maranhao R C, Abdalla D S. Evaluation of oxidative stress in patients with hyperlipidemia. Atherosclerosis 117(1):61-71, 1995
20. Huang J M, Huang Z X, Zhu W. Mechanism of high-density lipoprote in subfractions inhibiting copper-catalyzed oxidation of low-density lipoprotein. Clin Biochem 31(7):537-543, 1998
21. Cockerill G W et al. High-density lipoproteins rescue end-stage organ failure in a rat model of haemorraghic shock. J. Submicroscopic Cyt. Path. 32(3): 353, 2000

We claim:

1. A method for treatment of ischemia or reperfusion injury comprising administering to a subject in need thereof an effective amount of HDL.

2. The method of claim 1 wherein the ischemia or reperfusion injury is selected from the group consisting of ischemic stroke, ischemic tissue injury, cardiac ischemia, and cardiac reperfusion injury.

3. The method of claim 1 wherein HDL is administered by intravenous infusion and/or injection.

4. The method of claim 1 wherein HDL is administered before the start of ischemia and/or during ischemia.

5. The method of claim 1 wherein HDL is administered at or after reperfusion.

6. The method of claim 1 wherein HDL is administered in a dosage of from 10-200 mg HDL (weight based on apolipoprotein) per kg body weight per treatment.

7. The method of claim 1 wherein HDL is administered as a bolus injection and/or as an infusion.

8. The method of claim 1 wherein the HDL has a molar ratio of protein to phospholipid in the range of 1:50-1:250 and optionally additional lipids present in a molar ratio of protein to additional lipid of up to 1:20.

9. The method of claim 1, wherein HDL is administered in combination with other pharmaceutical agents.

10. The method of claim 1, wherein the HDL is selected from nascent HDL, reconstituted HDL (rHDL), recombinant HDL or mixtures thereof.

11. The method of claim 1, wherein the subject is a human.

12. The method of claim 1 wherein the HDL is administered after an ischemic event.

13. A method for reducing injury resulting from ischemia or reperfusion comprising administering an effective amount of HDL to a subject prior to an ischemic or reperfusion event.

* * * * *